United States Patent [19]

Fischer, deceased

[11] 3,963,479

[45] June 15, 1976

[54] HERBICIDE MIXTURES OF 3-LOWER ALKYL-2,1,3-BENZOTHIADIAZINONE-(4)-2,2-DIOXIDES OR SALTS THEREOF AND 4-HALOBUTYNYL-N-HALOPHENYL CARBAMATES

[75] Inventor: Adolf Fischer, deceased, late of Mutterstadt, Germany, by Caecilia Emma Fischer, legal representative

[73] Assignee: BASF Aktiengesellschaft, Ludwigshafen (Rhine), Germany

[22] Filed: Mar. 17, 1975

[21] Appl. No.: 559,321

Related U.S. Application Data

[60] Continuation-in-part of Ser. No. 432,685, Jan. 11, 1974, abandoned, which is a division of Ser. No. 343,629, March 22, 1973, Pat. No. 3,888,655.

[30] Foreign Application Priority Data

Apr. 13, 1972  Germany............................ 2217722

[52] U.S. Cl. ........................................ 71/91; 71/111
[51] Int. Cl.² ............................................ A01N 9/12
[58] Field of Search ................................ 71/91, 111

[56] References Cited
UNITED STATES PATENTS 2,906,614   9/1959   Hopkins et al...................... 71/111

3,708,277   1/1973   Zeidler et al. ......................... 71/91

OTHER PUBLICATIONS

Fischer, "Herbicidal Compositions," (1971) CA 74, no. 110, 714w, (1971).

Fischer, "Herbicidal Compositions, etc.;" (1971) CA 75, no. 75217h, (1971).

*Primary Examiner*—Glennon H. Hollrah
*Attorney, Agent, or Firm*—Johnston, Keil, Thompson & Shurtleff

[57] ABSTRACT

Herbicide compositions of mixtures in the weight ratio of 5:1 to 1:5 of (a) 3-lower alkyl-2,1,3-benzothiadiazinone-(4)-2,2-dioxide or a salt thereof and (b) a compound of the formula

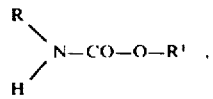

where R denotes halophenyl and $R^1$ denotes haloalkynyl of 4 carbon atoms.

8 Claims, No Drawings

HERBICIDE MIXTURES OF 3-LOWER ALKYL-2,1,3-BENZOTHIADIAZINONE-(4)-2,2-DIOXIDES OR SALTS THEREOF AND 4-HALOBUTYNYL-N-HALOPHENYL CARBAMATES

RELATED APPLICATION

This application is a continuation-in-part of application Ser. No. 432,685, filed Jan. 11, 1974, now abandoned, which in turn is a division of application Ser. No. 343,629, filed Mar. 22, 1973, now U.S. Pat. No. 3,888,655, the disclosures of which are incorporated herein by reference.

The present invention relates to a herbicide comprising a composition of several active ingredients.

It is known that substituted phenyl ethers, carbamates, terephthalates, acid amides, benzoic acids, fluorenecarboxylic acids and benzothiadiazinones have a herbicidal action. However, this action is poor.

It has been found that a composition of
a. a compound of the formula where R denotes lower alkyl of a maximum of 4 carbon atoms, or its salts, such as alkali metal, alkaline earth metal, ammonium, hydroxyalkylammonium, alkylammonium and hydrazine salts, e.g. salts with sodium, lithium, potassium, calcium, iron, methylammonium, trimethylammonium, ethylammonium, diethanolammonium, ethanolammonium, dimethylamine, dimethylethanolamine, hydrazine and phenylhydrazine, and
b. a compound of the formula $$\begin{array}{c} R \\ \diagdown \\ N-CO-O-R^1 \\ \diagup \\ H \end{array}$$

where denotes halophenyl and $R^1$ denotes haloalkynyl of 4 carbon atoms, e.g. 4-chlorobutynyl, have a herbicidal action superior to that of their individual components.

Active ingredients $a$ to $b$ may be applied to amounts of 0.5 to 5 kg per hectare.

The weight ratio of $a : b$ is from 5:1 to 1:5, preferably from 3:1 to 1:3.

The compositions of the invention are suitable for controlling unwanted plants, e.g. dicotyledonous seed weeds, monocotyledonous grassy seed weeds and Cyperaceae in crops such as cereals, rice, soybeans, Indian corn, potatoes, peas, and beans.

The compositions may be used pre- and/or postemergence.

The agents according to the invention may be used as solutions, emulsions, suspensions oil dispersions, granules or dusts. The form of application depends entirely on the purpose for which the agents are being used; in any case it should ensure a fine distribution of the active ingredient.

For the preparation of solutions to be sprayed direct, mineral oil fractions of medium to high boiling point, such as kerosene or diesel oil, further coal-tar oils and oils of vegetable or mineral origin, and cyclic hydrocarbons such as tetrahydronaphthalene and alkylated naphthalenes are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, wetting agent, adherent, emulsifying or dispersing agent and possibly solvent. Oils of various types may be added to ready-to-use spray liquors.

Dusts may be prepared by mixing or grinding the active ingredients with a solid carrier, e.g., clay or fertilizers.

Granules may be prepared by bonding the active ingredients to solid carriers.

Directly sprayable dispersions may also be prepared with oils.

The new compounds may be mixed with fertilizers, insecticides, fungicides and other herbicides.

EXAMPLE 1

The plants wheat (*Triticum aestivum*), barley (*Hordeum vulgare*), wild oats (*Avena fatua*), slender foxtail (*Alopecurus myosuroides*), catchweed bedstraw (*Galium aparine*), chickweed (*Stellaria media*) and henbit (*Lamium amplexicaule*) were treated at a growth height of 4 to 20 cm with the following amounts of the following individual active ingredients and compositions thereof, each active ingredient and each composition being emulsified or dispersed in 500 liters of water per hectare:

I 4-chlorobutyn-2-yl-1 N-3-chlorophenylcarbamate, 1 and 2 kg per hectare;
II 5-chloro-4-methyl-2-propionamide thiazole, 2 and 3 kg per hectare;
III 3,5-dibromo-4-hydroxybenzaldoxime-O-(2',4'-dinitrophenyl)-ether, 0.75 and 1.5 kg per hectare;
IV 9-hydroxyfluorenecarboxylic acid-(9), 1 and 3 kg per hectare;
V 3-isopropyl-2,1,3-benzothiadiazinone-(4)-2,2-dioxide, 0.75, 1.5, 2 and 3 kg per hectare;
I + V 1.0 + 1.0 kg per hectare;
II + V 2.0 + 1.0 kg per hectare;
III + V 0.75 + 0.75 kg per hectare;
IV + V 1.0 + 2.0 kg per hectare.

After 8 to 12 days it was acertained that the compositions had a better overall action than the individual active ingredients, combined with good crop plant compatibility. The results are given below:

| Active ingredient kg/ha | I | | II | | III | | IV | | V | | | | I+V | II+V | III+V | IV+V |
|---|---|---|---|---|---|---|---|---|---|---|---|---|---|---|---|---|
| | 1 | 2 | 2 | 3 | 0.75 | 1.5 | 1 | 3 | 0.75 | 1 | 1.5 | 2 | 3 | 1+1 | 2+1 | 0.75+0.75 | 1+2 |
| Triticum aestivum | 0 | 0 | 10 | 20 | 0 | 10 | 0 | 0 | 0 | 0 | 0 | 0 | 0 | 0 | 10 | 0 | 0 |
| Hordeum vulgare | 0 | 0 | 10 | 20 | 5 | 15 | 0 | 15 | 0 | 0 | 0 | 0 | 0 | 10 | 0 | 0 | |

-continued

| Active ingredient kg/ha | I 1 | I 2 | II 2 | II 3 | III 0.75 | III 1.5 | IV 1 | IV 3 | V 0.75 | V 1 | V 1.5 | V 2 | V 3 | I+V 1+1 | II+V 2+1 | III+V 0.75+0.75 | IV+V 1+2 |
|---|---|---|---|---|---|---|---|---|---|---|---|---|---|---|---|---|---|
| Avena fatua | 70 | 90 | 50 | 70 | — | — | — | — | 5 | 5 | 5 | 15 | 10 | 85 | 80 | — | — |
| Alopecurus myosuroides | 60 | 85 | 50 | 75 | — | — | — | — | 5 | 5 | 10 | 10 | 15 | 80 | 80 | — | — |
| Galium aparine | 5 | 10 | 30 | 45 | 20 | 45 | 30 | 85 | 35 | 40 | 60 | 70 | 80 | 80 | 90 | 90 | 100 |
| Stellaria media | 10 | 30 | 40 | 65 | 30 | 70 | 30 | 90 | 40 | 60 | 70 | 90 | 90 | 90 | 100 | 100 | 100 |
| Lamium amplexicaule | 5 | 10 | 5 | 10 | 45 | 80 | 30 | 95 | 30 | 40 | 50 | 60 | 70 | 75 | 75 | 100 | 100 |

0 = no damage
100 = complete destruction

EXAMPLE 2

In the greenhouse, various plants were treated at a growth height of from 3 to 18 cm with the following amounts of the following individual active ingredients and compositions thereof as emulsions, dispersions, aqueous solutions or tankmix solutions:

I  3-isopropyl-2,1,3-benzothiadiazinone-(4) -2,2-dioxide, 0.5, 0.75, 1 and 1.5 kg/ha;

II  3-isopropyl-2,1,3-benzothiadiazinone-(4)-2,2-dioxide, sodium salt, 0.5, 0.75, 1 and 1.5 kg/ha;

III  3-isopropyl-2,1,3-benzothiadiazinone-(4)-2,2-dioxide, dimethylamine salt, 0.5, 0.75, 1 and 1.5 kg/ha;

IV  3-isopropyl-2,1,3-benzothiadiazinone-(4)-2,2-dioxide, diethanolamine salt, 0.5, 0.75, 1 and 1.5 kg/ha;

V  4-chlorobutyn-2-yl-1 N-3-chlorophenylcarbamate, 0.5, 0.75, 1 and 1.5 kg/ha;

I+V, II+V, III+V and IV+V each of these compositions at rates of 0.5+1, 1+0.5 and 0.75+0.75 kg/ha.

After 2 to 3 weeks it was ascertained that the compositions had a better herbicidal action than their components, combined with the same good crop plant compatibility.

The results are given below:

| Active ingredient kg/ha | I 0.5 | I 0.75 | I 1 | I 1.5 | II 0.5 | II 0.75 | II 1 | II 1.5 |
|---|---|---|---|---|---|---|---|---|
| Crop plants: | | | | | | | | |
| Triticum aestivum | 0 | 0 | 0 | 0 | 0 | 0 | 0 | 0 |
| Hordeum vulgare | 0 | 0 | 0 | 0 | 0 | 0 | 0 | 0 |
| Secale cereale | 0 | 0 | 0 | 0 | 0 | 0 | 0 | 0 |
| Unwanted plants: | | | | | | | | |
| Galium aparine | 30 | 35 | 40 | 60 | 30 | 40 | 45 | 60 |
| Avena fatua | 0 | 2 | 5 | 5 | 0 | 0 | 0 | 5 |

| Active ingredient kg/ha | III 0.5 | III 0.75 | III 1 | III 1.5 | IV 0.5 | IV 0.75 | IV 1 | IV 1.5 | V 0.5 | V 0.75 | V 1 | V 1.5 |
|---|---|---|---|---|---|---|---|---|---|---|---|---|
| Crop plants: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Galium aparine | 28 | 40 | 50 | 60 | 35 | 45 | 60 | 67 | 0 | 0 | 5 | 0 |
| Avena fatua | 0 | 0 | 0 | 0 | 0 | 0 | 0 | 0 | 40 | 60 | 70 | 80 |

0 = no damage
100 = complete destruction

| Active ingredient kg/ha | I+V 0.5 1 | I+V 1 0.5 | I+V 0.75 0.75 | II+V 0.5 1 | II+V 1 0.5 | II+V 0.75 0.75 | III+V 0.5 1 | III+V 1 0.5 | III+V 0.75 0.75 | IV+V 0.5 1 | IV+V 1 0.5 | IV+V 0.75 0.75 |
|---|---|---|---|---|---|---|---|---|---|---|---|---|
| Crop plants: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Gallium aparine | 80 | 87 | 80 | 76 | 90 | 80 | 70 | 90 | 80 | 86 | 100 | 92 |

| Active ingredient kg/ha | I+V | | | II+V | | | III+V | | | IV+V | | |
|---|---|---|---|---|---|---|---|---|---|---|---|---|
| | 0.5 / 1 | 1 / 0.5 | 0.75 / 0.75 | 0.5 / 1 | 1 / 0.5 | 0.75 / 0.75 | 0.5 / 1 | 1 / 0.5 | 0.75 / 0.75 | 0.5 / 1 | 1 / 0.5 | 0.75 / 0.75 |
| Avena fatua | 100 | 90 | 95 | 100 | 85 | 96 | 96 | 80 | 98 | 100 | 87 | 100 |

0 = no damage
100 = complete destruction

EXAMPLE 3

In the greenhouse, various plants were treated at a growth height of from 1 to 25 cm with the following amounts of the following individual active ingredients and compositions thereof as dispersions, emulsions or aqueous solutions:

After 2 to 3 weeks it was ascertained that the compositions had a better herbicidal action than their components, combined with the same crop plant compatibility.

The results are given below:

| Active ingredient kg/ha | I | | | | | II | | | | | III | | | | | IV | | | |
|---|---|---|---|---|---|---|---|---|---|---|---|---|---|---|---|---|---|---|---|
| | 0.5 | 1.5 | 2 | 2.5 | 3 | 0.5 | 1.5 | 2 | 2.5 | 3 | 0.5 | 1.5 | 2 | 2.5 | 3 | 0.5 | 1.5 | 2 | 2.5 | 3 |
| Crop plants: | | | | | | | | | | | | | | | | | | | | |
| Triticum aestivum | 0 | 0 | 0 | 0 | 0 | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 | 0 | 0 | 0 | 0 | 0 |
| Unwanted plants: | | | | | | | | | | | | | | | | | | | | |
| Galium aparine | 30 | 60 | 75 | 90 | 95 | 30 | 60 | 80 | 90 | 94 | 28 | 60 | 75 | 90 | 95 | 35 | 67 | 80 | 90 | 95 |
| Avena fatua | 0 | 5 | 7 | 9 | 10 | 0 | 5 | 7 | 10 | 10 | 0 | 0 | 3 | 6 | 10 | 0 | 0 | 2 | 5 | 10 |

0 = no damage
100 = complete destruction

| Active ingredient kg/ha | V | | | | | I + V | | | | II + V | | | |
|---|---|---|---|---|---|---|---|---|---|---|---|---|---|
| | 0.5 | 1.5 | 2 | 2.5 | 3 | 1.5 / 0.5 | 0.5 / 1.5 | 2.5 / 0.5 | 0.5 / 2.5 | 1.5 / 0.5 | 0.5 / 1.5 | 2.5 / 0.5 | 0.5 / 2.5 |
| Crop plants: | | | | | | | | | | | | | |
| Triticum oestivum | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 |
| Unwanted plants: | | | | | | | | | | | | | |
| Galium aparine | 0 | 8 | 10 | 15 | 20 | 100 | 86 | 100 | 95 | 100 | 82 | 100 | 95 |
| Avena fatua | 40 | 80 | 90 | 95 | 100 | 95 | 100 | 100 | 100 | 96 | 100 | 100 | 100 |

0 = no damage
100 = complete destruction

| Active ingredient kg/ha | III + V | | | | IV + V | | | |
|---|---|---|---|---|---|---|---|---|
| | 1.5 / 0.5 | 0.5 / 1.5 | 2.5 / 0.5 | 0.5 / 2.5 | 1.5 / 0.5 | 0.5 / 1.5 | 2.5 / 0.5 | 0.5 / 2.5 |
| Crop plants: | | | | | | | | |
| Triticum oestivum | 0 | 0 | 0 | 0 | 0 | 0 | 0 | 0 |
| Hordeum vulgare | 0 | 0 | 0 | 0 | 0 | 0 | 0 | 0 |
| Secale cereale | 0 | 0 | 0 | 0 | 0 | 0 | 0 | 0 |
| Unwanted plants: | | | | | | | | |
| Galium aparine | 100 | 80 | 100 | 97 | 100 | 90 | 100 | 98 |
| Avena fatua | 93 | 100 | 100 | 100 | 95 | 100 | 100 | 100 |

0 = no damage
100 = complete destruction

I  3-isopropyl-2,1,3-benzothiadiazinone-(4)-2,2-dioxide

II  3-isopropyl-2,1,3-benzothiadiazinone-(4)-2,2-dioxide, sodium salt

III  3-isopropyl-2,1,3-benzothiadiazinone-(4)-2,2-dioxide, dimethylamine salt

IV  3-isopropyl-2,1,3-benzothiadiazinone-(4)-2,2-dioxide, diethanolamine salt

V  4-chlorobutyn-2-yl-1 N-3-chlorophenylcarbamate each of these compounds at rates of 0.5, 1.5, 2, 2.5 and 3 kg/ha;

I + V, II + V, III + V and IV + V, each at rates of 0.5 + 1.5, 1.5 + 0.5, 2.5 + 0.5 and 0.5 + 2.5 kg/ha.

I claim:

1. A herbicide composition comprising an inert carrier having dispersed therein a herbicidally effective amount of a mixture of herbicides consisting essentially of a. a compound of the formula

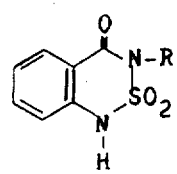

where R denotes lower alkyl of a maximum of 4 carbon atoms, or an alkali metal, alkaline earth metal, ammonium, lower alkylammonium, lower hydroxyalkylammonium, or hydrazine salt thereof, and b. a compound of the formula

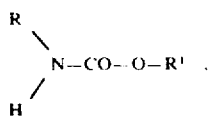

where R denotes chlorophenyl and $R^1$ denotes 4-chlorobutynyl in a weight ratio of $a:b$ of 5:1 to 1:5.

2. A composition as claimed in claim 1 wherein R in compound a is isopropyl.

3. A composition as claimed in claim 1 wherein R in compound a is isopropyl, and compound b is 4-chlorobutyn-2-yl-1-N-3-chlorophenylcarbamate.

4. A herbicide composition as claimed in claim 3 wherein said weight ratio is 3:1 to 1:3.

5. A herbicide composition as claimed in claim 2 wherein said weight ratio is 3:1 to 1:3.

6. A herbicide composition as claimed in claim 1 wherein said weight ratio is 3:1 to 1:3.

7. A herbicide composition as claimed in claim 1 wherein compound a is 3-isopropyl-2,1,3-benzothiadiazinone-(4)-2,2-dioxide or the sodium, dimethylamine, or diethanolamine salt thereof.

8. A herbicide composition as claimed in claim 1 wherein compound a is 3-isopropyl-2,1,3-benzothiadiazinone-(4)-2,2-dioxide or the sodium, dimethylamine, or diethanolamine salt thereof, and compound b is 4-chlorobutyn-2-yl-1 N-3-chlorophenylcarbamate.

* * * * *